United States Patent [19]

Ross

[11] Patent Number: 4,738,619
[45] Date of Patent: Apr. 19, 1988

[54] METHODS AND APPARATUS FOR SELECTING A DENTAL ANCHOR

[75] Inventor: Stanley E. Ross, Boca Raton, Fla.

[73] Assignee: Ross Systems Corporation, Palm Beach, Fla.

[21] Appl. No.: 934,651

[22] Filed: Nov. 25, 1986

[51] Int. Cl.$^4$ ............................................. A61C 19/04
[52] U.S. Cl. ..................................... 433/72; 433/173; 433/229
[58] Field of Search ............ 433/229, 68, 69, 70, 433/71, 72, 173; 400/697

[56] References Cited

U.S. PATENT DOCUMENTS

| | | | |
|---|---|---|---|
| 3,942,621 | 3/1976 | Karlan | 400/697 |
| 4,289,848 | 9/1981 | Miller et al. | 433/72 |
| 4,431,416 | 2/1984 | Niznick | |
| 4,571,180 | 2/1986 | Kulick | 433/72 |

OTHER PUBLICATIONS

Photocopies of Types of Rub-Off Transfer Sheets by Letraset U.S.A. Inc. of Paramus, N.J. (8 pgs.).

Primary Examiner—John J. Wilson
Assistant Examiner—Rohini Sarma
Attorney, Agent, or Firm—Burns, Doane, Swecker & Mathis

[57] ABSTRACT

The selection of a dental anchor for insertion into a jaw bone of a patient is achieved utilizing a transparent transfer sheet carrying on a first side thereof a plurality of removable pictorial representations of dental anchors of different sizes. The transfer sheet is superimposed over an X-ray to position different ones of the pictorial representations over a site of the X-ray where a dental implant is to be installed. When a pictorial representation of desired size has been selected, a second side of the transfer sheet opposite the selected pictorial representation is rubbed in order to transfer the selected pictorial representation onto the X-ray. Each of the pictorial representations includes indicia indicative of a dimension of the associated anchor. The pictorial representations are magnified in size relative to the X-ray to provide a factor of safety.

6 Claims, 2 Drawing Sheets

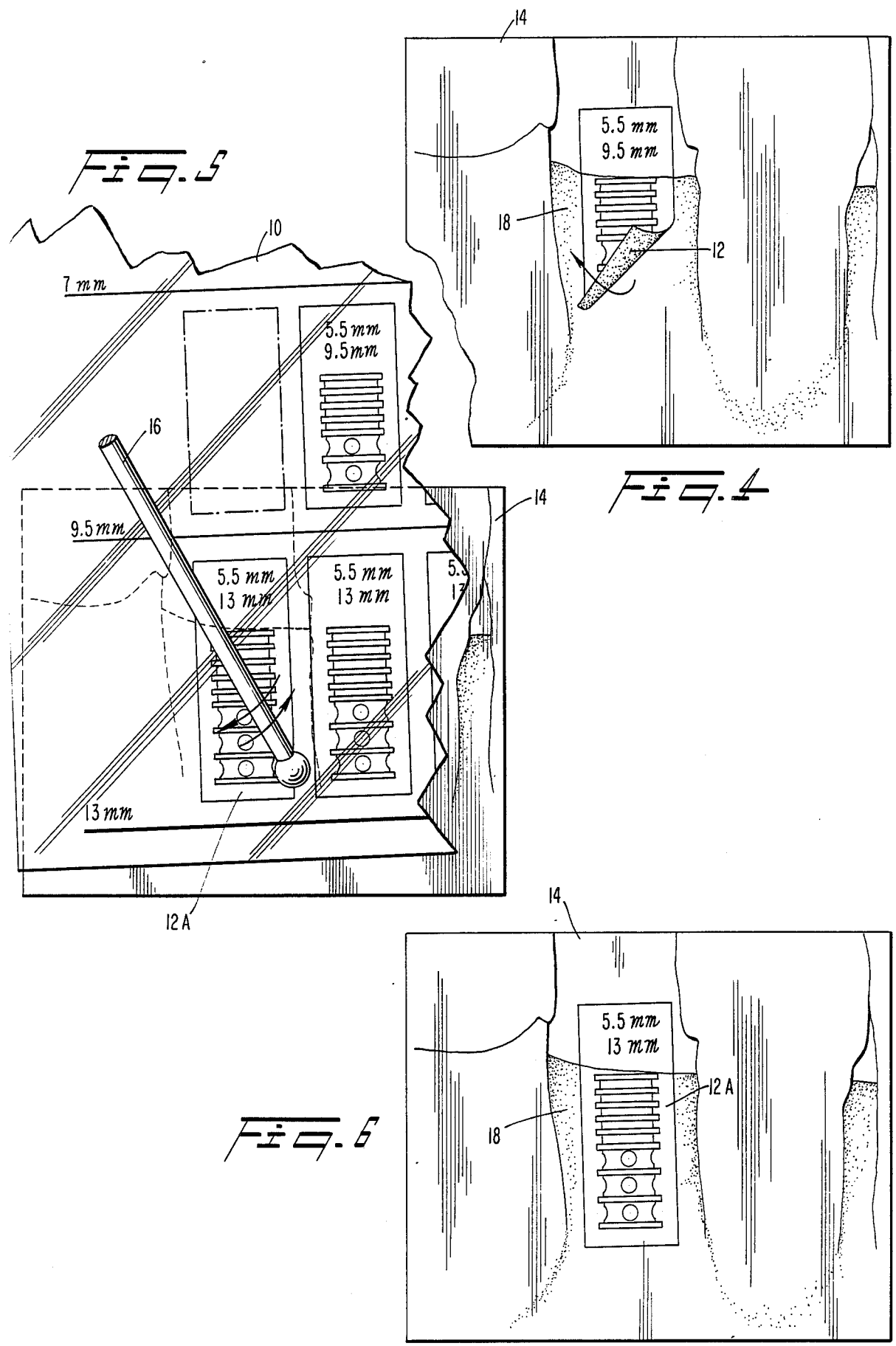

METHODS AND APPARATUS FOR SELECTING A DENTAL ANCHOR

BACKGROUND AND OBJECTS OF THE INVENTION

The present invention relates to the installation of dental prostheses into a patient's jaw bone and, in particular, to methods and apparatus for selecting a suitably sized dental anchor.

One technique for the installation of dental prostheses involves drilling a bore into a patient's jaw bone and inserting a dental anchor into the bore. Eventually, bone tissue grows against the anchor to fixedly secure the anchor in place. Attention is directed to the disclosures in copending U.S. application Ser. Nos. 896,101 and 896,524 both filed Aug. 13, 1986, for a more detailed disclosure of such a procedure.

It is important that an anchor of proper size (i.e., proper diameter and length) be selected. Various factors influence the size selection of the anchor, such as the amount of space at the anchor site between existing teeth, the width (thickness) of the patient's jaw bone at the anchor site, the depth of the jaw bone, and the proximity of nerves which must be avoided during the drilling procedure.

One present practice for the selection of anchors involves the use of a transparent sheet which contains pictorial reproductions of anchors of various size. That sheet is placed in an X-ray view box along with a patient's X-ray, and the various pictorial reproductions of anchors on the sheet are sequentially placed in overlying relationship to the anchor site on the X-ray, until a proper anchor size is determined. The pictorial reproductions of the anchors and the X-ray are of the same magnification. Presently available sheets of this type carry pictorial representations of anchors which are at 25 percent magnification and are instructed to be used in conjunction with X-rays which are at 52 percent magnification.

Such a practice requires a considerable amount of skill and care since the transparent sheet includes indicia in addition to the reproductions of the anchors which can interfere with a full clear viewing of the X-ray. Also, after the procedure is performed, there remains no permanent pictorial record which can be re-checked and verified at a later period prior to the installation of the anchor into the patient's jaw bone or which can be compared to a later X-ray after the anchor installation procedure has been completed.

SUMMARY OF THE INVENTION

One aspect of the present invention relates to a method of selecting a dental anchor of suitable size for insertion into a jaw bone of a patient. The method includes the step of providing an X-ray of a patient's jaw bone including a site where a dental implant is to be installed. A transparent transfer sheet is superimposed over the X-ray. The transfer sheet carries on a first side thereof, a plurality of removable pictorial representations of dental anchors of different sizes. Different ones of the pictorial representations are positioned over the site of the X-ray until a pictorial representation of desired size has been selected. That selected pictorial representation is arranged over the size of the X-ray in facing relationship to the X-ray. A second side of the transfer sheet opposite the selected pictorial representation is rubbed to transfer the selected pictorial representation onto the site of the X-ray.

Preferably, each of the pictorial representations includes indicia indicative of a dimension of the associated anchor, and that indicia is transferred to the site of the X-ray along with the pictorial representation.

Preferably, the removable pictorial representations are magnified in size relative to the X-ray, in order to incorporate a factor of safety into the method.

Another aspect of the present invention involves the transparent transfer sheet carrying on a first side thereof a plurality of removable pictorial representations of dental anchors of different sizes. The pictorial representations include indicia indicative of a dimension of a represented anchor, there being a plurality of pictorial representations for each anchor size. A selected pictorial representation is transferrable to a receiver sheet by arranging one side of a transfer sheet against the receiver sheet and rubbing on a second side of a transfer sheet opposite the selected pictorial representation.

Preferably, the pictorial representations are magnified in size with respect to the respective anchors.

BRIEF DESCRIPTION OF THE DRAWINGS

The objects and advantages of the invention will become apparent from the following detailed description of a preferred embodiment thereof in connection with the accompanying drawings, in which like numerals designate like elements, and in which:

FIG. 4 is a view similar to FIG. 3 as the pictorial representation is being removed from the X-ray;

FIG. 5 is a view similar to FIG. 2 as a different pictorial representation is being transferred to the X-ray; and FIG. 6 is a view similar to FIG. 4 after the different pictorial representation has been transferred to the X-ray.

DETAILED DESCRIPTION OF A PREFERRED EMBODIMENT OF THE INVENTION

Figure 1:
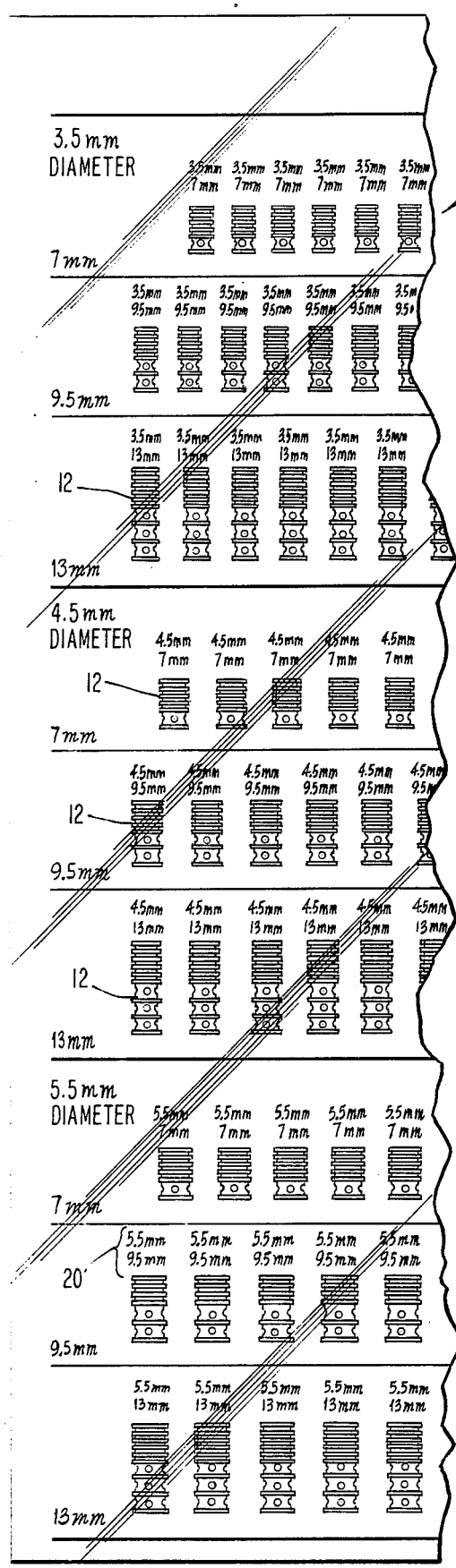
FIG. 1 is a fragmentary plan view of a transparent transfer sheet according to the present invention.
Figure 2:
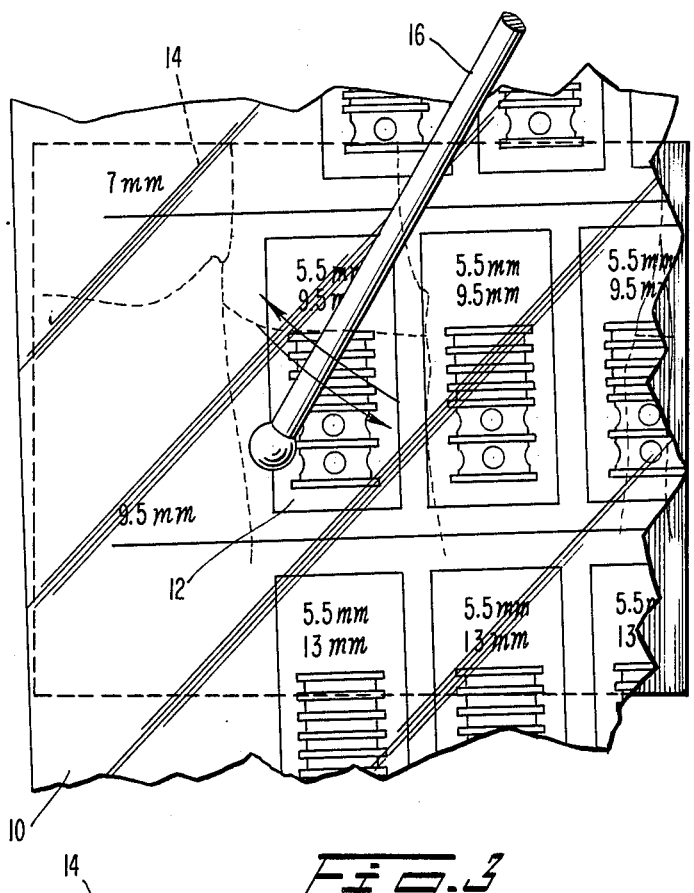
FIG. 2 is a plan view of a portion of the transfer sheet positioned in superimposed relationship to an X-ray as a pictorial representation is being rubbed off the transfer sheet and onto the X-ray.
Figure 3:
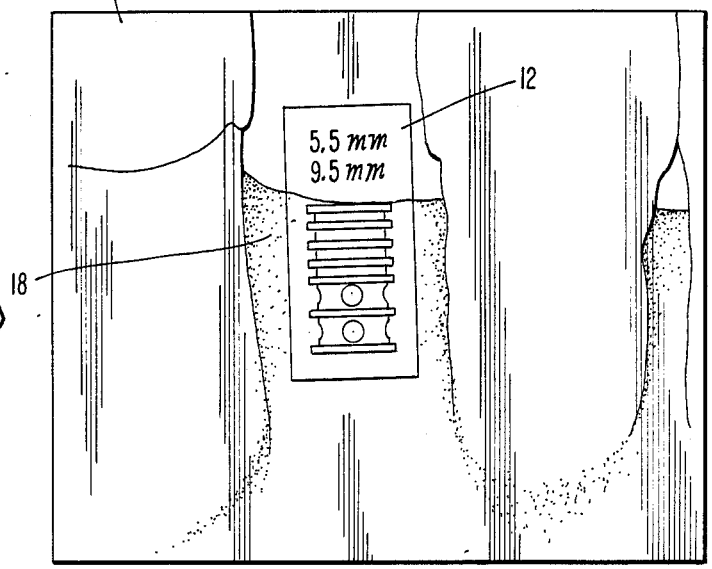
FIG. 3 is a plan view of the X-ray after the pictorial representation has been attached thereto.

In accordance with the present invention there is utilized a transparent transfer sheet 10, or acetate overlay, on which are provided a plurality of removable pictorial representations of dental anchors 12 of various sizes. Each pictorial representation can be rubbed off the transfer sheet by placing the sheet upon a receiver sheet, with the pictorial representation facing the receiver sheet 14. The opposite side of the transfer sheet overlying the pictorial representation to be transferred is rubbed with a blunt object 16, causing the pictorial representation to be transferred to the receiver sheet.

The receiver sheet 14 comprises an X-ray of a patient's jaw bone. The pictorial representation of an anchor is transferred to the site 18 on the X-ray where the anchor is to be installed. The transfer sheet is then removed to enable the technician to clearly inspect the X-ray to ensure that the selected anchor is of suitable size for the anchor site. The accuracy of this inspection is not adversely affected by the presence of additional indicia which could interfere with a clear viewing of the X-ray, as can occur in the case of conventional transparent overlays. If the technician feels that a different anchor might be more suitable, the technician simply peels off the transferred pictorial representation 12 (FIG. 4) and applies a pictorial representation 12A of different size (FIGS. 5, 6).

A plurality of available anchor sizes are represented on the transfer sheet, with a plurality of pictorial representations of each size being provided so that the sheet can be used repeatedly. Each pictorial representation includes indicia 20 indicative of dimensions of the respective anchor, such as diameter and length.

It will be appreciated that once the desired anchor has been transferred to the X-ray, the X-ray constitutes a permanent pictorial record of the selected anchor, identified by dimensions 20, for future reference and verification.

Furthermore, in order to provide a factor of safety in the anchor selection process, the pictorial representations 12 are of greater magnification than the X-ray 14. Thus, as long as the selected pictorial representation fits within the anchor site 18, it is assured that the corresponding anchor can safely be employed, even if the size of the selected pictorial representation was of borderline acceptability. For example, if the X-ray is at full-scale, the pictorial representations will be magnified, preferably by about 25 percent. On the other hand, if the X-ray is magnified, then the pictorial representations will be of yet greater magnification. For example, if the X-ray is at 25 percent magnification, the pictorial representations would be of about 50 percent magnification.

Transparent transfer sheets of the type in which pictures or other indicia can be transferred to a receiver sheet are well known and are available from various sources such as a company called Chartpak, One River Road, Leeds, Massachusetts. Thus, in accordance with the present invention, pictorial representations of anchors and dimensional indicia are utilized as the items to be transferred.

Although the present invention has been described in connection with a preferred embodiment thereof, it will be appreciated by those skilled in the art that additions, modifications, substitutions, and deletions not specifically described may be made without departing from the spirit and scope of the invention as defined in the appended claims.

What is claimed is:

1. A method of selecting a dental anchor of suitable size for insertion into a jaw bone of a patient, comprising the steps of:
    providing an X-ray of a patient's jaw bone including a site where a dental implant is to be installed,
    superimposing over said X-ray a transparent transfer sheet carrying on a first side thereof a plurality of removable pictorial representations of dental anchors of different sizes,
    positioning different ones of said pictorial representations over said site of said X-ray until a pictorial representation of desired size has been selected,
    arranging said selected pictorial representation over said site of said X-ray in facing relationship thereto,
    rubbing a second side of said transfer sheet opposite said selected pictorial representation to transfer said selected pictorial representation onto said site of said X-ray, and
    selecting a dental anchor in accordance with said transferred pictorial representation.

2. A method according to claim 1, wherein each of said pictorial representations includes indicia indicative of a dimension of the associated anchor, said indicia being transferred to said site of said X-ray along with said pictorial representation.

3. A method according to claim 1, wherein said superimposing step comprises superimposing over said X-ray a transfer sheet carrying a plurality of each size of pictorial representations of each anchor size, so that said sheet is reusable.

4. A method according to claim 1, wherein said superimposing step comprises superimposing over said X-ray a transfer sheet carrying a plurality of removable pictorial representations which are magnified in size relative to said X-ray.

5. A transparent transfer sheet carrying on a first side thereof a plurality of removable pictorial representations of dental anchors of different sizes, including indicia indicative of a dimension of the represented anchors, there being a plurality of pictorial representation for each anchor size, a selected pictorial representation being transferrable to a receiver sheet by arranging said one side of said transfer sheet againt the receiver sheet and rubbing on a second side of said transfer sheet opposite said selected pictorial representation, said pictorial representation being magnified in size with respect to the respective anchors.

6. A transparent transfer sheet according to claim 5, wherein said indicia is indicative of diameter and length of the respective anchors.

* * * * *